United States Patent
Leininger et al.

(10) Patent No.: US 10,080,519 B2
(45) Date of Patent: Sep. 25, 2018

(54) METHODS AND APPARATUSES FOR DETECTION AND CLASSIFICATION OF SEIZURES USING EMG SENSORS

(71) Applicant: Brain Sentinel, Inc., San Antonio, TX (US)

(72) Inventors: Peter A. Leininger, San Antonio, TX (US); Jason T. Getman, San Antonio, TX (US); Michael R. Girouard, Shavano Park, TX (US); Russell M. Herring, San Antonio, TX (US); Jose E. Cavazos, San Antonio, TX (US)

(73) Assignee: Brain Sentinel, Inc., San Antonio, TX (US)

( * ) Notice: Subject to any disclaimer, the term of this patent is extended or adjusted under 35 U.S.C. 154(b) by 0 days.

(21) Appl. No.: 15/429,009

(22) Filed: Feb. 9, 2017

(65) Prior Publication Data

US 2017/0215786 A1    Aug. 3, 2017

Related U.S. Application Data

(63) Continuation of application No. 14/686,475, filed on Apr. 14, 2015, now Pat. No. 9,603,573.

(60) Provisional application No. 61/979,225, filed on Apr. 14, 2014.

(51) Int. Cl.
| | |
|---|---|
| *A61B 5/00* | (2006.01) |
| *A61B 5/01* | (2006.01) |
| *A61B 5/0402* | (2006.01) |
| *A61B 5/0488* | (2006.01) |
| *A61B 5/1455* | (2006.01) |
| *A61B 5/11* | (2006.01) |

(52) U.S. Cl.
CPC .......... *A61B 5/4094* (2013.01); *A61B 5/0022* (2013.01); *A61B 5/01* (2013.01); *A61B 5/0402* (2013.01); *A61B 5/0488* (2013.01); *A61B 5/1116* (2013.01); *A61B 5/14551* (2013.01); *A61B 5/6802* (2013.01); *A61B 5/6824* (2013.01); *A61B 5/7282* (2013.01); *A61B 5/746* (2013.01)

(58) Field of Classification Search
CPC ....... A61B 5/746; A61B 5/022; A61B 5/0488; A61B 5/4094; A61B 5/6824
USPC .......................................... 600/301
See application file for complete search history.

(56) References Cited

U.S. PATENT DOCUMENTS

| | | | | |
|---|---|---|---|---|
| 2008/0281638 A1* | 11/2008 | Weatherly | ............ | G06F 19/322 705/3 |
| 2012/0029390 A1* | 2/2012 | Colborn | ............... | A61B 5/0245 600/595 |
| 2013/0095459 A1* | 4/2013 | Tran | ..................... | A61B 5/6816 434/247 |

(Continued)

*Primary Examiner* — Paula J Stice
(74) *Attorney, Agent, or Firm* — Pizarro Allen PC (57) ABSTRACT

A system for monitoring a patient for seizure activity may include one or more detection units. The detection units may include one or more electromyography sensors configured to evaluate a patient for seizure activity. The detection units may further include one or more sensors configured to detect an orientation of the patient and/or when a sensor is bearing a portion of the patient's weight or otherwise pressed against the patient. In some embodiments, methods of detection may include adjusting an algorithm for seizure detection based on a recognition of whether a muscle is constrained or whether the muscle is free to move.

19 Claims, 6 Drawing Sheets

(56) References Cited

U.S. PATENT DOCUMENTS

2013/0116514 A1* 5/2013 Kroner .................... A61B 7/00
600/301

* cited by examiner

METHODS AND APPARATUSES FOR DETECTION AND CLASSIFICATION OF SEIZURES USING EMG SENSORS

CROSS REFERENCE TO RELATED APPLICATIONS

This application claims priority to U.S. Provisional Patent Application No. 61/979,225 filed Apr. 14, 2014. The disclosure of U.S. Provisional Patent Application No. 61/979,225 is herein fully incorporated by reference.

BACKGROUND

A seizure may be characterized as abnormal or excessive synchronous activity in the brain. At the beginning of a seizure, neurons in the brain may begin to fire at a particular location. As the seizure progresses, this firing of neurons may spread across the brain, and in some cases, many areas of the brain may become engulfed in this activity. Seizure activity in the brain may cause the brain to send electrical signals through the peripheral nervous system to different muscles the activation of which may initiate a redistribution of ions within muscle fibers.

Techniques designed for studying and monitoring seizures have typically relied upon electroencephalography (EEG), which characterizes electrical signals using electrodes attached to the scalp or head region of a seizure prone individual or seizure patient. In EEG electrodes may be positioned so as to measure such activity; that is, electrical activity originating from neuronal tissue. Alternatively, electromyography (EMG) may be used for seizure detection. In EMG an electrode may be placed on or near the skin, over a muscle, to detect electrical signals from muscle fiber activation.

Detecting an epileptic seizure using electroencephalography (EEG) typically requires attaching many electrodes and associated wires to the head and using amplifiers to monitor brainwave activity. The multiple EEG electrodes may be very cumbersome and generally require some technical expertise to apply and monitor. Furthermore, confirming a seizure requires observation in an environment provided with video monitors and video recording equipment. Unless used in a staffed clinical environment, such equipment is frequently not intended to determine if a seizure is in progress but rather provide a historical record of the seizure after the incident. Such equipment is usually meant for hospital-like environments where a video camera recording or caregiver's observation may provide corroboration of the seizure, and is typically used as part of a more intensive care regimen such as a hospital stay for patients who experience multiple seizures. A hospital stay may be required for diagnostic purposes or to stabilize a patient until suitable medication can be administered. Upon discharge from the hospital, a patient may be sent home with little further monitoring. However, at any time after being sent home the person may experience another seizure, perhaps fatal.

A patient should in some cases be monitored at home for some length of time in case another seizure should occur. Seizures with motor manifestations may have patterns of muscle activity that include rhythmic contractions of some, most, or all of the muscles of the body. A seizure could, for example, result in Sudden Unexplained Death in Epilepsy (SUDEP). The underlying causes of SUDEP are not well understood; however, some possible mechanisms causing SUDEP may include tonic activation of the diaphragm muscle so as to prevent breathing, neurogenic pulmonary edema, asystole, and other cardiac dysrhythmia. If a sleeping person experiences a seizure involving those conditions, then caregivers may not be aware that the seizure is occurring, and thus be unable to render timely aid.

While there presently exist ambulatory devices for diagnosis of seizures, they are EEG-based and are generally not designed or suitable for long-term home use or daily wearability. Other seizure alerting systems may operate by detecting motion of the body, usually the extremities. Such systems may generally operate on the assumption that while suffering a seizure, a person will move erratically and violently. For example, accelerometers may be used to detect violent extremity movements. However, depending upon the type of seizure, this assumption may or may not be true. Electrical signals sent from the brain during the seizure are frequently transmitted to many muscles simultaneously, which may result in muscles fighting each other and effectively canceling out violent movement. In other words, the muscles may work to make the person rigid rather than cause actual violent movement. Thus, the seizure may not be consistently detected with accelerometer-based detectors.

Accordingly, there is a need for an epileptic seizure method and apparatus that can be used in a non-institutional or institutional environment without many of the cumbersome electrodes to the head or extremities. Such an apparatus may be minimally intrusive, minimally interfere with daily activities and be comfortably used while sleeping. There is also a need for an epileptic seizure method and apparatus that accurately detects a seizure with motor manifestations and may alert one or more local and/or remote sites of the presence of a seizure. Furthermore, there is a need for an epileptic detection seizure method and apparatus that may be used in a home setting and which may provide robust seizure detection, even in the absence of violent motion, and which may be personalizable, e.g., capable of being tailored for an individual or specific population demographic.

SUMMARY

In some embodiments, a method of monitoring a patient for seizure activity may include coupling a first EMG sensor to a muscle located on the left side of the patient's body, coupling a second EMG sensor to a muscle located on the right side of the patient's body, and monitoring the patient by collecting and analyzing EMG signal from each of the first and the second sensor. A response may be initiated if either the first sensor or the second sensor indicates EMG activity indicative of a seizure.

A method of monitoring a patient for seizure activity may include coupling at least one EMG sensor to a muscle located on the patient's body, wherein the EMG sensor is part of a detection unit that includes at least one sensor element configured to determine how the muscle is oriented. And, further including, monitoring the patient by collecting EMG signals from the EMG sensor and collecting data associated with the orientation of the muscle. The collected signal may be analyzed together with the muscle orientation data to determine if seizure activity is present and whether to initiate a response.

A detection unit configured for analyzing an EMG sensor for the presence of seizure activity including at least one microelectromechanical sensor element configured to determine the orientation of the detection unit.

DETAILED DESCRIPTION

The apparatuses and methods described herein may be used to detect seizures and timely alert caregivers of seizure-related events. The apparatuses may include sensors attached to a patient or patient's clothing and may be configured for measurement of muscle electrical activity using electromyography (EMG). Detection of seizures using EMG electrodes is further described, for example, in Applicant's U.S. patent application Ser. Nos. 13/275,309 and 13/542,596 and Applicant's U.S. Provisional Patent Application Nos. 61/875,429, 61/894,793, and 61/969,660, the disclosures of each of which are herein fully incorporated by reference. As described herein, in some embodiments, a patient may be monitored for seizure activity using a monitoring system that may include sensors included within at least two detection units. For example, sensors may be included in separate detection units that may be attached on opposite sides of the body, and the monitoring system may be configured to collect EMG electrical activity, analyze the collected signal for seizure activity, and send an alarm if a seizure is detected. A monitoring system may, for example, be configured to initiate a response if either or both of muscles on the patient's left or right side are suitably activated to show seizure activity, and in some embodiments, a detected event may be classified based on symmetry or lack of symmetry in activity between the left and rights sides of a patient's body. In some embodiments, signals collected from sensors on the left and right side of a patient's body may be used to classify an event as a complex partial seizure. In some embodiments, detection units may include one or more elements configured to measure the position and/or orientation of the units over time and that information may, in some embodiments, be further sent along with EMG data.

The monitoring systems described herein may, in some embodiments, include at least two detection units. At least one detection unit may be configured for placement on either the left or right side of a patient's body. In addition, at least one other detection unit may be configured for placement on the other side of a patient, i.e., approximately opposite to the first detection unit. A detection unit may, for example, be woven into a shirt sleeve mounted to an armband or bracelet or otherwise held against a patient's body and attached on or near a muscle of the body, such as by using a support frame around the detection device, elastic band, and/or adhesive material. And, in some embodiments a sensor may be implanted. A detection unit may, for example, be attached, coupled, or placed on or near muscle of a patient's arms or legs. By way of nonlimiting example, a detection unit may, in some embodiments, be placed on or near a patient's biceps, triceps, hamstrings, quadriceps, or other suitable muscle. A detection unit may be configured such that it may be suitably placed near a specific muscle (or muscle group) or body part or otherwise designated for placement on an appropriate muscle. For example, in some embodiments, a given detection unit may be labeled or marked to ensure that the detection unit is coupled to a specified muscle, muscle group, and/or specific side of the body. Signals from a detection unit may be sent, preferably wirelessly, to one or more computers separate from the detection unit and the signals may, in some embodiments, be sent with an identification signal for the detection unit. Therefore, signals may be identified as being provided from either the left or right side of the body and/or from a specific muscle or group of muscles.

In some embodiments, a monitoring system may also include one or more detection units where the position, orientation, or both of the one or more detection units may be determined. In some embodiments, the detection unit may include one or more components useful to determine the position or orientation of the device such as with respect to a reference position or orientation. A detection unit may include, for example, and without limitation, one or more GPS sensors, accelerometers, gyroscopes, magnetometers, or combinations of elements thereof. Any number of the aforementioned elements may be included in one or more orientation and/or position sensors included in a detection unit. And, in some embodiments, sensors in a detection unit may be used to determine the orientation of one or more sides or parts of a detection unit. For example, one or more sensors may be configured to determine whether a side of the detection unit, e.g., a side adjacent muscle, is oriented facing up or facing down. And, one or more sensors may be configured to determine whether the patient's body is or is not resting against the device. Position and/or orientation sensitive components may be configured to measure changes and/or absolute orientation of a detection unit or muscle to which the detection unit is attached or placed on. That is, elements suitable both to measure changes in orientation and or the absolute orientation (e.g., yaw, pitch, and/or roll) of a sensor with respect to a reference position may be included. In some embodiments, an orientation sensor may include one or more elements suitable to measure each of yaw, pitch, and roll and may comprise any number of one, two, or three axis sensor elements suitably configured. In preferred embodiments, a detection unit may include one or more solid state microelectromechanical (MEMS) gyroscopes or other solid state elements. Microelectromechanical (MEMS) gyroscopes may operate, for example, using a vibrating mechanical element to sense transfer of energy between vibrational modes of a structure, and changes in state from a reference position may then be determined as understood by those of ordinary skill in the art. Changes in orientation may be detected using any suitable technique such as, by way of nonlimiting example, by sensing changes in capacitive coupling of electrodes, piezoelectric, or electromagnetic effects. An orientation and/or position sensor may therefore collect information about a patient's position and/or orientation, e.g., whether a patient's muscle is oriented upwards or downwards. And, that information may, in some embodiments, be combined with EMG data to more clearly define the state of the patient at any time during monitoring such as at or near the time that an alarm may be sent including before or after sending of an alarm.

Detection using EMG is described in greater detail in Applicant's co-pending applications such as U.S. Ser. Nos. 13/275,309 and 13/542,596 already incorporated by reference herein. And, position and/or orientation data may be combined with EMG data collected as described therein or in other EMG detection systems. For example, in some embodiments, depending upon whether a detection unit is oriented horizontally or vertically the system may adjust one or more threshold settings and/or weighting factors in a detection algorithm. Thus, the system may be particularly calibrated for whether a muscle of a patient is in a certain orientation. And may, for example, be particularly calibrated based on whether a patient may be lying horizontally, lying horizontally with the patient's weight on the sensor, or oriented vertically.

In some embodiments, in general, EMG electrode signals may be collected and processed to determine the value of one or more seizure variables. A "seizure variable" may in some embodiments refer to a characteristic of one or more portions of data collected from the output signal of a detector that may be related to seizure activity. For a given set of data, the EMG data may be processed and a seizure variable may be measured and one or more numerical values may be associated with the measured seizure variable. For example, the amplitude of a signal may be a seizure variable that may have one or more numerical values associated with it for a given set of data. Amplitude may refer to either a level of signal, or absolute value of signal magnitude, as may be appropriate for a given calculation. Signals collected may, for example, be rectified, and EMG signal amplitude or intensity may refer to the magnitude of rectified signal from an EMG sensor. A value of a seizure variable may be compared to a threshold level and may be used to assess whether a characteristic is present and the presence or absence of the seizure variable may be an input in an algorithm for determining whether a seizure may have occurred. And, in some embodiments, the threshold value may be dependent upon whether a detection unit (and associated muscle) is in a particular orientation such as vertical or horizontal and/or whether a patient's weight is or is not pressed against a detection unit (and against the muscle to which the device is attached).

In some embodiments, a method of detecting seizures may comprise receiving an EMG signal and processing the EMG signal to determine whether a seizure variable is present. Apparatuses described herein for detecting seizures may comprise one or more EMG electrodes, preferably on each of at least two detection units, capable of providing an EMG signal substantially representing seizure-related muscle activity and a processor configured to receive the EMG signal, process the EMG signal to determine whether a seizure may be occurring, and generate an alert if a seizure is determined to be occurring.

Figure 1:
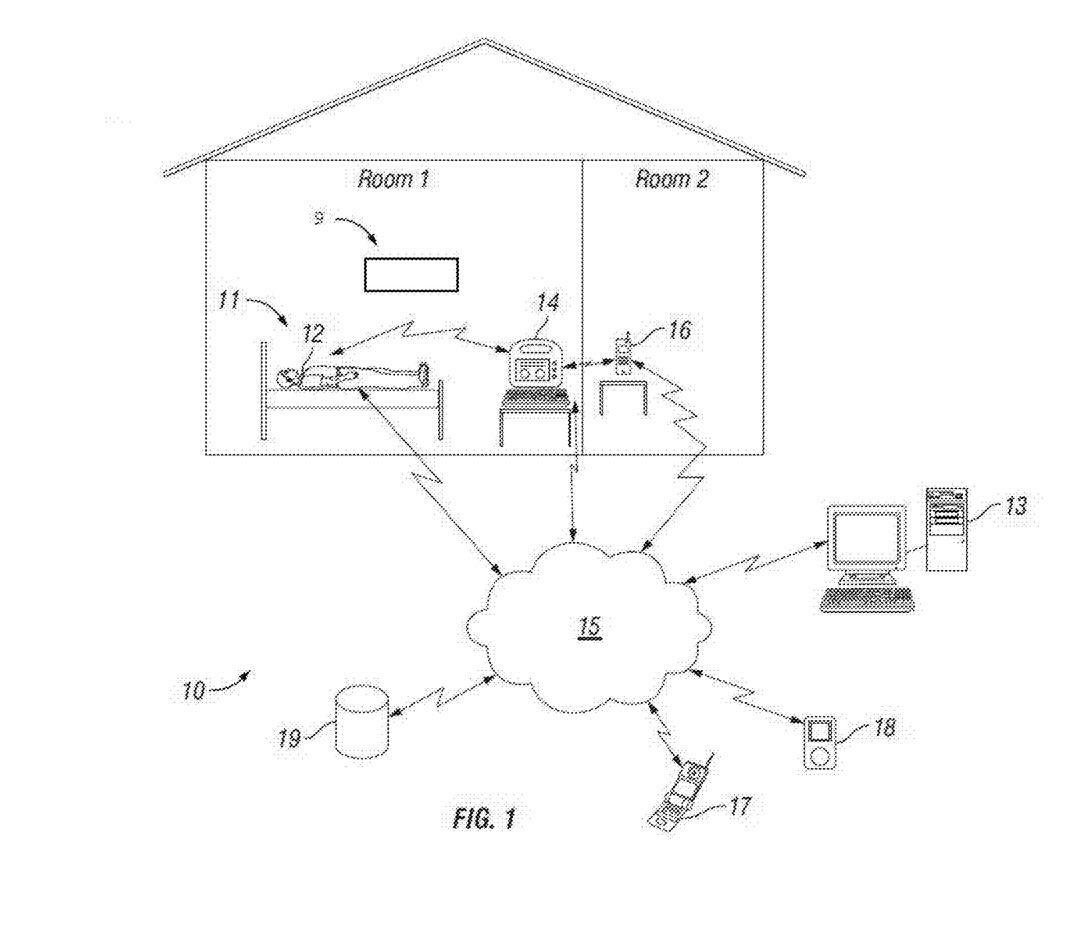
FIG. 1 illustrates one embodiment of a seizure detection system.

A variety of systems may be suitable for collecting large amounts of EMG and other patient-related data, organizing such data for system optimization, and for initiating an alarm in response to a suspected seizure. FIG. 1 illustrates an exemplary embodiment of such a system. In the embodiment of FIG. 1, a seizure detection system 10 may include a video camera 9, a detection unit 12, an acoustic sensor 13, a base station 14, and an alert transceiver 16. The detection unit may comprise one or more EMG electrodes capable of detecting electrical signals from muscles at or near the skin surface of a patient, and delivering those electrical EMG signals to a processor for processing. The EMG electrodes may be attached to a patient, and may, in some embodiments, be implanted within the tissue of a patient near a muscle that may be activated during a seizure. Implanted devices may, for example, be particularly amenable for some patients where EMG signals may typically be weak such as patients with significant adipose tissue. The base station may comprise a computer capable of receiving and processing EMG signals from the detection unit and/or acoustic data from an acoustic sensor, determining from the processed EMG and/or acoustic signals whether a seizure may have occurred, and sending an alert to a caregiver. An alert transceiver may be carried by, or placed near, a caregiver to receive and relay alerts transmitted by the base station. Other components that may be included in the system 10, including for example, an alert transceiver 16, wireless device 17, 18, storage database 19, electronic devices for detecting changes in the integrity of an electrode-to-skin interface, and one or more environmental transceivers are also described in Applicant's U.S. patent application Ser. Nos. 13/275,309 and 13/542,596 and Applicant's Provisional Application Nos. 61/894,793 and 61/875,429.

In using the apparatus of FIG. 1, for example, a person 11 susceptible to epileptic seizures may be resting in bed, or may be at some other location as daily living may include, and may have a detection unit 12 in physical contact with or in proximity to his or her body. The detection unit 12 may be a wireless device to allow a person to get up and walk around without having to be tethered to an immobile power source or to a bulkier base station 14. For example, the detection unit 12 may be woven into a shirt sleeve, may be mounted to an armband or bracelet, or may be an implanted device. In other embodiments, one or more detection units 12 may be placed or built into a bed, a chair, an infant car seat, or other suitable clothing, furniture, equipment and accessories used by those susceptible to seizures. The detection unit 12 may comprise a simple sensor, such as an electrode, that may send signals to the base station for processing and analysis, or may comprise a "smart" sensor having some data processing and storage capability. In some embodiments, a simple sensor may be connected via wire or wirelessly to a battery-operated transceiver mounted on a belt worn by the person.

The system may monitor the patient, for example, while resting, such as during the evening and nighttime hours. If the detection unit 12 on the patient detects a seizure, the detection unit 12 may communicate via wire or wirelessly, e.g., via a communications network or wireless link, with the base station 14 and may send some signals to the base station device for more thorough analysis. For example, the detection unit 12 may process and use EMG signals (and optionally ECG, temperature and/or audio sensor signals) to make an initial assessment regarding the likelihood of occurrence of a seizure, and may send those signals and its assessment to the base station 14 for separate processing and confirmation. If the base station 14 confirms that a seizure is likely occurring, then the base station 14 may initiate an alarm for transmission over the network 15 to alert a caregiver by way of email, text, or any suitable wired or wireless messaging indicator. It should be appreciated that the detection unit 12 may, in some embodiments, be smaller and more compact than the base station and it may be convenient to use a power supply with only limited strength. Therefore, it may be advantageous, in some embodiments, to control the amount of data that is transferred between the detection unit 12 and the base station 14 as this may increase the lifetime of any power supply elements integrated in the detection unit 12. In some embodiments, if one or more of the detection unit 12, the base station 14, or a caregiver, e.g., a remotely located caregiver monitoring signals provided from the base station, determines that a seizure may be occurring a video monitor 9 may be triggered to collect information.

In some embodiments, a single sensor may be used to monitor a patient for EMG activity. In other embodiments, at least two sensors may be attached to a patient. In some embodiments, sensors may be configured such that a patient when sleeping has at least one sensor that is not disposed between a surface of the bed and the patient's body. For example, the patient may have sensors on opposite arms such that if the patient sleeps on either the left or right sides of their body at least one sensor may typically not be disposed against the bed. Moreover, in some embodiments, a sensor may be configured to detect when it is bearing a portion of the patient's weight or otherwise pressed against the patient, as may be typical for a patient that is, for example, side sleeping. A sensor may, for example, include a pressure sensor. For some patients and in some resting positions such as with a muscle constrained, the muscle may respond differently to motor stimulation than, for example, when the muscle is free to move. Apparatuses herein may sense when a sensor is under pressure and evaluate when a muscle electrical signature is likely to have originated from a constrained muscle. In some embodiments, a sensor may adjust a treatment algorithm based on the recognition of such a constraint (e.g., lowering a threshold value if muscle is constrained), and if two or more sensors are present the system may, for example, use only data from the sensor positioned over or near the unconstrained muscle that may most reliably detect seizure. For example, the system may collect data from a sensor electrode attached to muscle that is not hindered during motor activation.

The base station 14, which may be powered by a typical household power supply and contain a battery for backup, may have more processing, transmission and analysis power available for its operation than the detection unit 12, may be able to store a greater quantity of signal history, and evaluate a received signal against that greater amount of data. The base station 14 may communicate with an alert transceiver 16 located remotely from the base station 14, such as in the bedroom of a family member, or to a wireless device 17, 18 carried by a caregiver or located at a work office or clinic. The base station 14 and/or transceiver 16 may send alerts or messages to caregivers, or medical personnel via any suitable means, such as through a network 15 to a cell phone 17, PDA 18 or other client device. The system 10 may thus provide an accurate log of seizures, which may allow a patient's physician to understand more quickly the success or failure of a treatment regimen. Of course, the base station 14 may simply comprise a computer having installed a program capable of receiving, processing and analyzing signals as described herein, and capable of transmitting an alert. In other embodiments, the system 10 may simply comprise, for example, EMG electrodes and a smartphone, such as an iPhone, configured to receive EMG signals from the electrodes for processing the EMG signals as described herein using an installed program application. In further embodiments, so-called "cloud" computing and storage may be used via network 15 for storing and processing the EMG signals and related data. In yet other embodiments, one or more EMG electrodes could be packaged together as a single unit with a processor capable of processing EMG signals as disclosed herein and sending an alert over a network. In other words, the apparatus may comprise a single item of manufacture that may be placed on a patient and that does not require a base station separate transceiver. Or, the base station may be a smartphone or tablet.

In the embodiment of FIG. 1, the signal data may be sent to a remote database 19 for storage. In some embodiments, signal data may be sent from a plurality of epileptic patients to a central database 19 and "anonymized" to provide a basis for establishing and refining generalized "baseline" sensitivity levels and signal characteristics of an epileptic seizure. The database 19 and base station 14 may be remotely accessed via network 15 by a remote computer 13 to allow updating of detector unit and/or base station software, and data transmission. The base station 14 may generate an audible alarm, as may a remote transceiver 16. All wireless links may be two-way for software and data transmission and message delivery confirmation. The base station 14 may also employ one or all of the messaging methods listed above for seizure notification. The base station 14 may provide an "alert cancel" button to terminate the incident warning.

In some embodiments, a transceiver may additionally be mounted within a unit of furniture or some other structure, e.g., an environmental unit or object. If a detection unit is sufficiently close to that transceiver, such a transceiver may be capable of sending data to a base station. Thus, the base station may be aware that information is being received from that transducer, and therefore the associated environmental unit. In some embodiments, a base station may select a specific template file, e.g., such as including threshold values and other data as described further herein, that is dependent upon whether or not it is receiving a signal from a certain transceiver. Thus, for example, if the base station receives information from a detector and from a transducer that is associated with a bed or crib it may treat the data differently than if the data is received from a transducer associated with another environmental unit, such as, for example, clothing typically worn while an individual may be exercising or an item close to a users sink where for example a patient may brush their teeth. More generally, a monitoring system may, in some embodiments, be configured with one or more elements with global positioning (GPS) capability, and position information may be used to adjust one or more routines that may be used in a detection algorithm.

The embodiment of FIG. 1 may be configured to be minimally intrusive to use while sleeping or minimally interfere in daily activities, may require a minimum of electrodes such as one or two, may require no electrodes to the head, may detect a seizure with motor manifestations, may alert one or more local and/or remote sites of the presence of a seizure, and may be inexpensive enough for home use.

Figure 2:
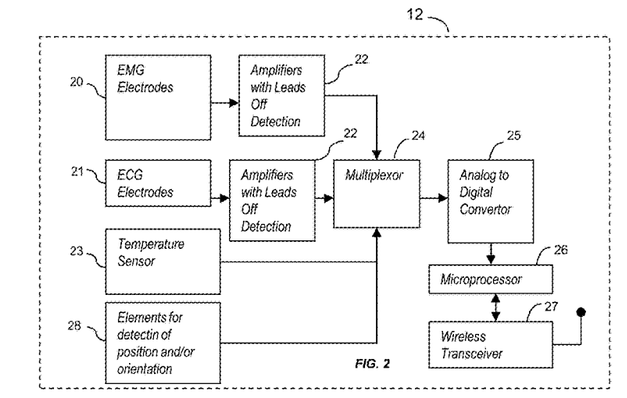
FIG. 2 illustrates one embodiment of a detection unit for a seizure detection system.

FIG. 2 illustrates an embodiment of a detection unit 12 or detector. The detection unit 12 may include EMG electrodes 20, and may also include ECG electrodes 21. The detection unit 12 may further include amplifiers with leads-off detectors 22. In some embodiments, one or more leads-off detectors may provide signals that indicate whether the electrodes are in physical contact with the person's body, or otherwise too disconnected from the person's body to adequately detect muscle activity, temperature, brain activity or other patient phenomena. The detection unit may further include one or more elements (28), such as solid state MEMS structures, configured for detection of position and/or orientation of the detection unit. For example, an element 28 may include one or more micromachined inertial sensors such as may include one or more gyroscopes, accelerometers, magnetometers or combinations thereof.

The detection unit 12 may further include a temperature sensor 23 to sense the person's temperature. Other sensors (not shown) may be included in the detection unit, as well, such as accelerometers, microphones, and sensors for oxygen saturation. Signals from electrodes 20 and 21, temperature sensor 23 and other sensors may be provided to a multiplexor 24. The multiplexor 24 may be part of the detection unit 12 or may be part of the base station 14 if the detection unit 12 is not a smart sensor. The signals may then be communicated from the multiplexor 24 to one or more analog-to-digital converters 25. The analog-to-digital converters may be part of the detection unit 12 or may be part of the base station 14. The signals may then be communicated to one or more microprocessors 26 for processing and analysis as disclosed herein. The microprocessors 26 may be part of the detection unit 12 or may be part of the base station 14. The detection unit 12 and/or base station 14 may further include memory of suitable capacity. The microprocessor 26 may communicate signal data and other information using a transceiver 27. Communication by and among the components of the detection unit 12 and/or base station 14 may be via wired or wireless communication.

Of course, the exemplary detection unit of FIG. 2 may be differently configured. Many of the components of the detector of FIG. 2 may be in base station 14 rather than in the detection unit 12. For example, the detection unit may simply comprise an EMG electrode 20 in wireless communication with a base station 14. In such an embodiment, A-D conversion and signal processing may occur at the base station 14. If an ECG electrode 21 is included, then multiplexing may also occur at the base station 14.

In another example, the detection unit 12 of FIG. 2 may comprise an electrode portion having one or more of the EMG electrode 20, ECG electrode 21 and temperature sensor 23, in wired or wireless communication with a small belt-worn transceiver portion. The transceiver portion may include a multiplexor 24, an A-D converter 25, microprocessor 26, transceiver 27 and other components, such as a memory and I/O devices (e.g., alarm cancel buttons and visual display).

Figure 3:
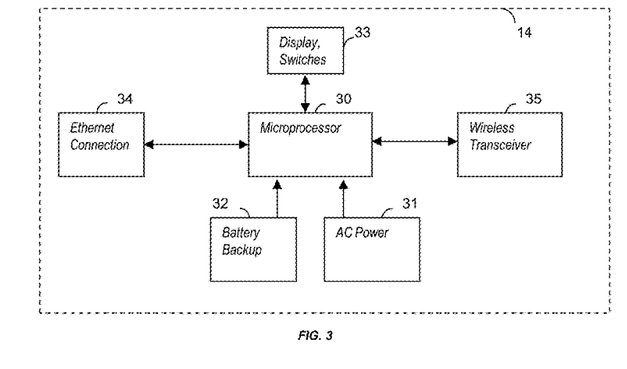
FIG. 3 illustrates one embodiment of a base station.

FIG. 3 illustrates an embodiment of a base station 14 that may include one or more microprocessors 30, a power source 31, a backup power source 32, one or more I/O devices 33, and various communications means, such as an Ethernet connection 34 and transceiver 35. The base station 14 may have more processing and storage capability than the detection unit 12, and may include a larger electronic display for displaying EMG signal graphs for a caregiver to review EMG signals in real-time as they are received from the detection unit 12 or historical EMG signals from memory. The base station 14 may process EMG signals and other data received from the detection unit 12. If the base station 14 determines that a seizure is likely occurring, it may send an alert to a caregiver via transceiver 35.

Various devices in the apparatus of FIGS. 1-3 may communicate with each other via wired or wireless communication. The system 10 may comprise a client-server or other architecture, and may allow communication via network 15. Of course, the system 10 may comprise more than one server and/or client. In other embodiments, the system 10 may comprise other types of network architecture, such as a peer-to-peer architecture, or any combination or hybrid thereof.

Figure 4:
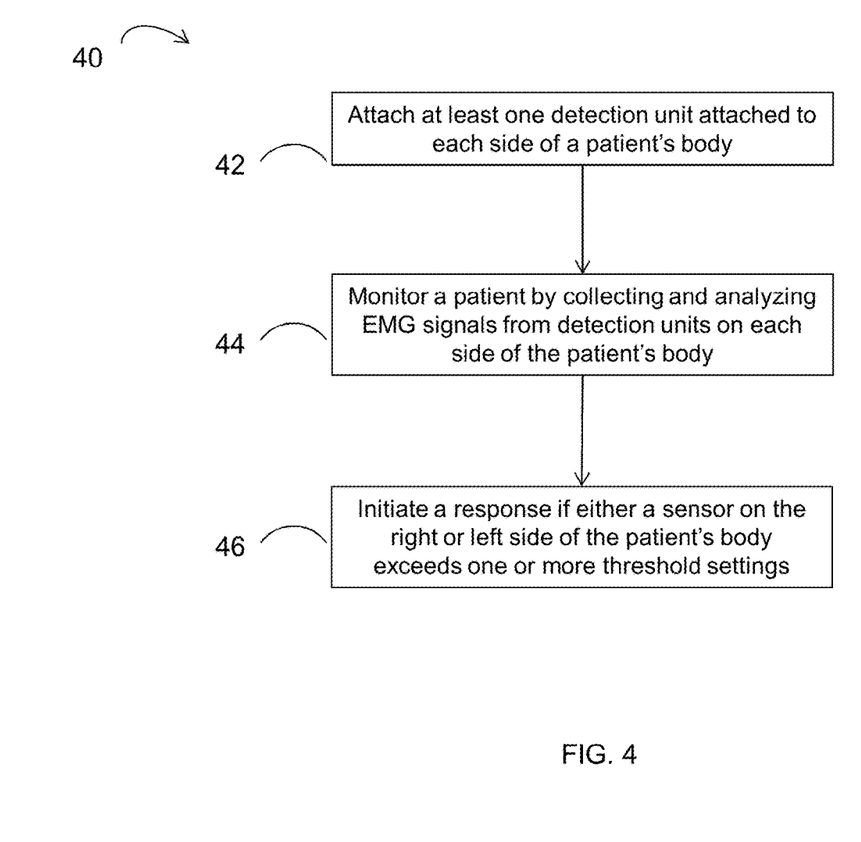
FIG. 4 illustrates one embodiment of a method for monitoring a patient for seizure related activity.

FIG. 4 illustrates an exemplary embodiment of a method 40 of monitoring EMG data for characteristics of seizure activity, and initiating a response if a seizure is detected. In a step 42, a patient or caregiver may attach a detection unit to at least one muscle on each side of the patient's body. In the step 44, the method 40 may include collecting and analyzing EMG signals from detection units on each side of the patient's body. And, in the step 46, if EMG data indicates that a seizure may be present a response may be initiated. For example, in the embodiment of the method 40, a response may be initiated if either of a sensor on the right or left side of the patient's body exceeds one or more thresholds.

Some seizure activity may selectively affect or significantly affect only one side of a patient, i.e., the activity may be asymmetric. And, if only a single sensor is placed on the patient a seizure may be missed because a side where muscles are suitably activated to detect the seizure may not have an attached sensor. Therefore, and particularly for patients prone to asymmetric seizures, it may be useful to include each of at least one left-side detection device and at least one right-side detection device. In some embodiments, information may be sent along with an alarm that indicates whether the right and left-side detection devices were each activated to about the same level, i.e., whether the seizure shows symmetric activity or asymmetric activity. In some embodiments, information related to the symmetry of seizure data may be stored and analyzed and threshold settings may be adjusted for a patient. For example, it may be learned that a patient typically exhibits different behavior for seizures that affect the left and right sides of their body, and that optimal threshold settings for detection of seizure activity may be different for sensors on the left and right sides of the patient. In addition, the severity of a seizure and or the likelihood that an emergency response should be sent may be related to whether a seizure is felt on either or both sides of a patient. In some embodiments, signals collected from right and left-side detection devices may be used to determine if a seizure may be classified as a complex partial seizure. For example, a seizure may be classified as a complex partial seizure if an amplitude signal collected from a detection device on one side of the body is more than a specified amount (e.g., about 50%) greater than an amplitude signal collected from a detection device on the other side of the body. In some embodiments, if a sensor is suitably configured, data associated with whether a sensor may have been under pressure, such as if the patient was lying on the side to which the sensor was attached, may be captured along with a classification of symmetry or lack of symmetry between collected signals.

Figure 5:
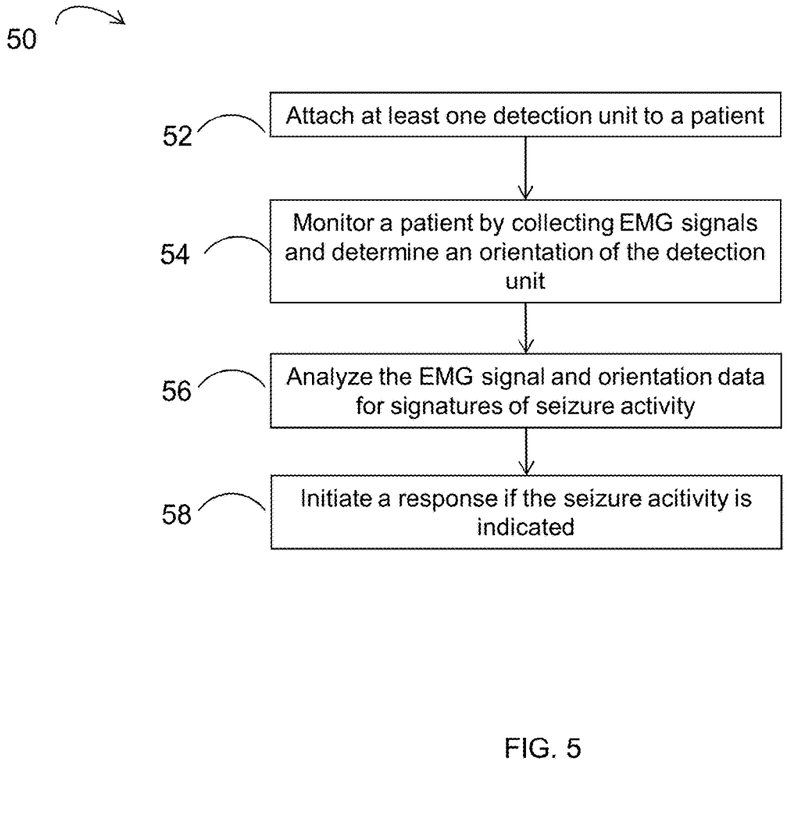
FIG. 5 illustrates another embodiment of a method for monitoring a patient for seizure related activity.

FIG. 5 illustrates another exemplary embodiment of a method 50 of monitoring EMG data for characteristics of seizure activity, and initiating a response if a seizure is detected. In a step 52 a patient or caregiver may attach at least one detection unit to a patient. And, in some embodiments, each of a left and right-side detection unit may be attached. In the exemplary embodiment of method 50, the detection unit (or units) may include one or more elements suitable to measure changes and/or the absolute orientation of the detection unit or individual parts or faces of the detection unit. In the step 54, a patient may be monitored by collecting EMG signals as well as information associated with the orientation of the detection unit. In the step 56, the EMG and orientation data may be analyzed for signatures of seizure activity. And, in the step 58, if seizure activity is indicated a response to detection may be initiated.

EMG and other information regarding the orientation of sensors in a detection unit may be combined in various ways. For example, referring to the step 56, analysis of signals may include applying one or more thresholds to the EMG data, and in some embodiments, particular thresholds may be dependent on the orientation of the sensor during or immediately before detection of seizure activity. In some embodiments, a response to a detected event may be dependent upon whether or not a patient was or is determined to be in a certain state. For example, a response may depend upon whether the patient is or was lying flat, standing, or in another state before, during, or after detection of seizure activity. Therefore, position, movement, and orientation information may be used to either adjust sensitivity settings, modify a response to a detected event, or both. And in some embodiments, information provided about the orientation and position of sensors may further be corroborated or analyzed together with other information including information associated with one or more environmental units or transceivers.

Figure 6A:
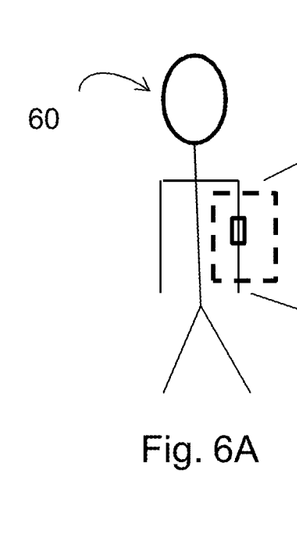
FIG. 6A shows a patient standing and with a detection unit attached to the patient.
Figure 6B:
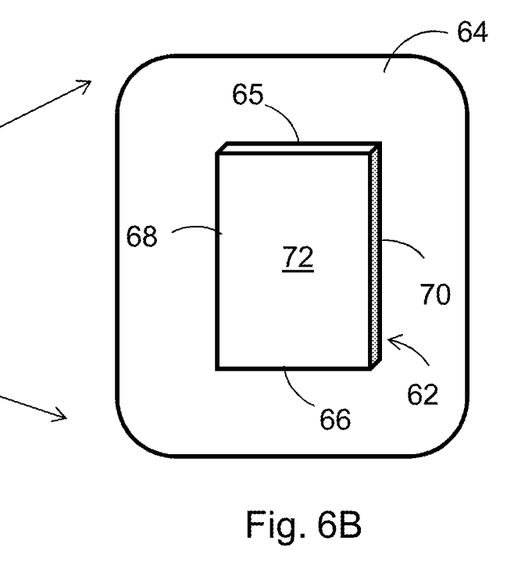
FIG. 6B shows the detection unit of FIG. 6A attached to the patient's skin and oriented vertically with respect to the ground.
Figures 7A, 7B:
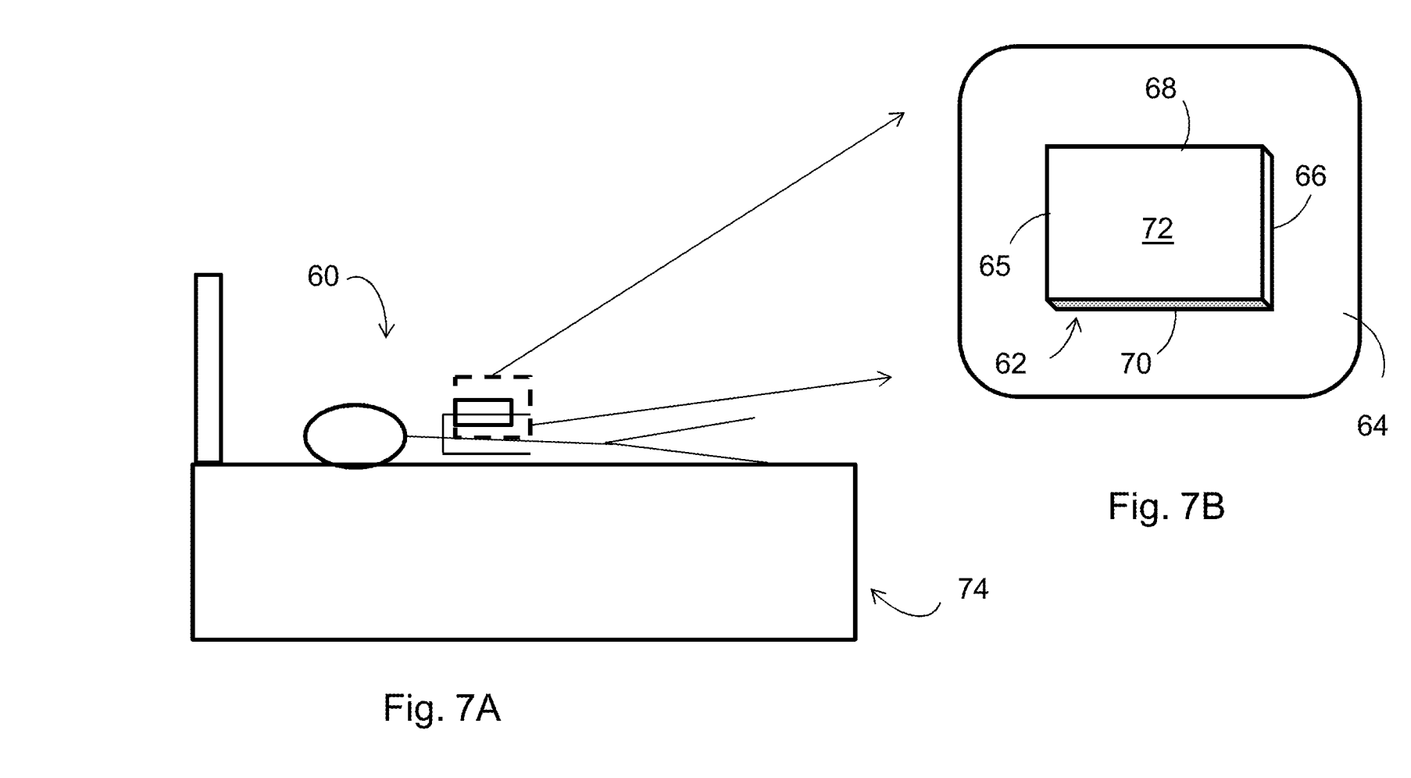
FIG. 7A shows a patient lying in bed and with a detection unit attached to the patient.
FIG. 7B shows the detection unit of FIG. 7A attached to the patient's skin and oriented horizontally with respect to the ground.

For example, it may be that a patient is in bed and a sensor placed, for example, on a muscle of the patients arm or upper arm may generally be aligned with a planar surface of the bed. Or, it may be that a patient is standing or otherwise propped up in another position. FIG. 6A shows a schematic representation of a patient 60 standing and wherein an arm of the patient may be or periodically adopt a position that orients the arm vertically, i.e., parallel to a normal vector from the ground. That is, as shown in FIG. 6B, a detection unit 62 is shown attached to a region of skin 64 which in this example may be the biceps or triceps of a patient's upper arm. Micromechanical sensor elements may be included in a detection unit on either or both of the face opposite the skin (72) and nearest the skin (not shown). The sensor elements may further be positioned at any of a top 65, a bottom 66, a first side 68 or a second side 70 of the detection unit 62. And based on signals from individual elements or the signals from elements as a whole it may be determined whether a patient is generally standing and or the arm are swinging back and forth such as may occur while the patient is walking. FIG. 7A shows the patient 60 lying in bed 74 and an expanded view of a portion of the patient's skin 64 and the attached detection unit 62 is shown in FIG. 7B. As shown therein and in comparison to FIG. 6B, sensor elements of the detection unit 62 may generally be oriented differently, and for example, the strength of vibrational modes of micromechanical sensor elements may indicate whether the detection unit is oriented as in FIG. 6B or FIG. 7B.

In some embodiments, a seizure event may be classified or thresholds may be applied in seizure analysis based on an orientation of the sensor during or immediately prior to a suspected seizure event. For example, the system may collect position information and it may be determined that immediately prior to a seizure a detection unit on the biceps, for example, was oriented vertically such as is common when a patient may be walking. Or, it may be determined that the patient was resting in bed with the biceps generally oriented horizontal to a surface of a bed. In some instances, a muscle may generally shake or jerk with a different resistance based on whether the arm or other body part is held vertically, horizontally, or at some other orientation, or if it may be constrained by contact with another surface, such as if sandwiched between a person's body and surface of a bed. And, in some embodiments herein that information may integrated into a detection algorithm.

In some events, it may be determined that the detection unit rapidly changed position, such as may occur if the patient experienced a fall. That information may be captured for example, if a muscle was oriented vertically before a seizure and horizontally after initial motor manifestations are detected. Therefore, position and/or orientation information for a detection unit may, in some cases, be used to determine a likelihood that a patient may have fallen. And, in some embodiments, the likelihood of a fall may be further corroborated if the detection unit experienced a rapid change in the magnitude or direction of acceleration during the course of a suspected seizure. And, in some embodiments, a dedicated accelerometer may be included in a sensor suitable for detecting transient accelerations and to correlate acceleration data with EMG data.

Although the disclosed method and apparatus and their advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition, or matter, means, methods and steps described in the specification. Use of the word "include," for example, should be interpreted as the word "comprising" would be, i.e., as open-ended. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods or steps.

What is claimed is:

1. A method of monitoring a patient for seizure activity comprising:
   placing a detection unit over a muscle located on said patient's body, said detection unit including at least one EMG sensor, at least one orientation sensor, and at least one pressure sensor;
   wherein said at least one orientation sensor is configured to determine how said muscle is oriented with respect to the ground;
   wherein said at least one pressure sensor is configured to indicate if a weight of said patient is pressed against said at least one pressure sensor;
   collecting EMG signals from said at least one EMG sensor;
   collecting orientation data from said at least one orientation sensor;
   collecting pressure data from said at least one pressure sensor; and
   analyzing the EMG signal, said orientation data, and said pressure data to determine if a seizure is detected and whether to initiate a response;
   wherein the detection of said seizure is calibrated based on whether the patient is lying substantially horizontally, lying substantially horizontally with the patient's weight on said one or more pressure sensor, or oriented substantially vertically.

2. The method of claim 1 wherein said response includes an emergency alarm response.

3. The method of claim 1 wherein said response includes sending a warning signal to a caregiver.

4. The method of claim 1 wherein the analyzing the EMG signals includes comparing a value for at least one seizure characteristic to a threshold value; and
   wherein said threshold value is dependent upon the orientation of said muscle during monitoring.

5. The method of claim 1 wherein the response is based on whether said patient was determined to be prone or engaged in a non-prone activity at a start of said seizure.

6. The method of claim 1 wherein the response is based on whether orientation data indicates that said muscle was approximately vertically oriented with respect to the ground at a start of said seizure and approximately horizontally oriented after completion of said seizure.

7. A detection unit configured for monitoring a patient for a presence of seizure activity, said detection unit comprising:
one or more EMG sensors configured for measurement of muscle electrical activity; and
one or more pressure sensors configured for determining if a weight of a patient is being pressed against at least one of said one or more pressure sensors.

8. The detection unit of claim 7 further comprising a position sensor.

9. The detection unit of claim 7 further comprising an oxygen saturation sensor.

10. The detection unit of claim 7 wherein the detection unit is configured for placement over one of a patient's biceps, triceps, hamstrings, or quadriceps.

11. The detection unit of claim 7 wherein the detection unit is configured for placement over a muscle suitable for collecting muscle electrical activity indicative of a patient seizure.

12. The detection unit of claim 7 wherein the detection unit is configured to detect when the patient may be side sleeping, and to allow the patient to side sleep without sending an alarm in the absence of a detected seizure.

13. The detection unit of claim 7 wherein the detection unit is configured to detect when the patient may be side sleeping, and to adjust one or more EMG thresholds for detection of a seizure based on whether the patient may be side sleeping.

14. A method of monitoring a patient for seizure activity comprising:
placing a detection unit including an EMG sensor over a muscle located on one side of said patient's body, said detection unit including a pressure sensor;
collecting and analyzing an EMG signal from said EMG sensor;
collecting pressure sensor data using said pressure sensor;
determining whether said pressure sensor data indicates that a weight of said patient is pressed against said pressure sensor; and
determining whether said EMG signal meets one or more threshold values in order to detect a seizure;
wherein said one or more threshold values are dependent upon whether a portion of said patient's body is resting on said pressure sensor; and
initiating a response if a seizure is detected.

15. The method of claim 14 wherein said response includes an emergency alarm response.

16. The method of claim 14 wherein said response includes sending a warning signal to a caregiver.

17. The method of claim 14 wherein said detection unit includes a microelectromechanical element configured to determine an orientation of said detection unit.

18. The method of claim 17 wherein said orientation indicates whether the patient is lying in a substantially prone orientation or standing in a vertical orientation.

19. The method of claim 17 wherein said detection unit includes a position sensor.

* * * * *